(12) United States Patent
Taussig et al.

(10) Patent No.: US 8,298,995 B2
(45) Date of Patent: Oct. 30, 2012

(54) REPEATABLE PROTEIN ARRAYS

(75) Inventors: Michael John Taussig, Hildersham (GB); Mingyue He, Sawston (GB)

(73) Assignee: Babraham Institute, Cambridge (GB)

( * ) Notice: Subject to any disclaimer, the term of this patent is extended or adjusted under 35 U.S.C. 154(b) by 794 days.

(21) Appl. No.: 11/916,976

(22) PCT Filed: Apr. 27, 2006

(86) PCT No.: PCT/GB2006/001550
§ 371 (c)(1),
(2), (4) Date: Jul. 16, 2008

(87) PCT Pub. No.: WO2006/131687
PCT Pub. Date: Dec. 14, 2006

(65) Prior Publication Data
US 2008/0293591 A1    Nov. 27, 2008

(30) Foreign Application Priority Data
Jun. 9, 2005 (GB) .................................. 0511717.1

(51) Int. Cl.
*C40B 50/06* (2006.01)
*C40B 50/16* (2006.01)
*C12Q 1/68* (2006.01)
*C40B 40/10* (2006.01)

(52) U.S. Cl. ............... 506/26; 506/18; 506/31; 435/6.1

(58) Field of Classification Search .................... 506/18, 506/26, 31; 435/6.1
See application file for complete search history.

(56) References Cited

U.S. PATENT DOCUMENTS

| 7,674,752 B2 * | 3/2010 | He et al. ........................ 506/26 |
| 2002/0192673 A1 * | 12/2002 | Labaer et al. ................... 435/6 |
| 2004/0161748 A1 * | 8/2004 | He et al. ........................ 435/6 |

FOREIGN PATENT DOCUMENTS

| WO | WO 02/14860 | 2/2002 |
| WO | WO 02/059601 | 8/2002 |

OTHER PUBLICATIONS

He et al., Nucleic Acids Research. vol. 29 (15): e73; 2001.*
Emili A. Q. & Cagney, G., "Large-scale functional analysis using peptide or protein arrays," *Nature Biotechnology*, 18(4) pp. 393-397 (2000).
Michaud, G. A. & Synder, M., "Proteomic Approaches for the Global Analysis of Proteins," *Biotechniques*, 33(6), pp. 1308-1316 (2002).

* cited by examiner

*Primary Examiner* — Amber D Steele
(74) *Attorney, Agent, or Firm* — Judy M. Mohr; McDermott Will & Emery

(57) ABSTRACT

The invention relates to a method of producing a protein array (5) on one support surface (3) from a corresponding nucleic acid array on a separate surface (1), to protein arrays produced by the method, to uses of the protein arrays in the identification of interactions between arrayed proteins and other molecules, and to kits for producing said protein arrays.

15 Claims, 6 Drawing Sheets

A B

REPEATABLE PROTEIN ARRAYS

This application is the U.S. national phase application of PCT International Application No. PCT/GB2006/001550, filed Apr. 27, 2006, which claims the benefit of priority under 35 U.S.C. §119(a) to Great Britain Patent Application No. 200511717, filed Jun. 9, 2005.

The invention relates to a method of producing a protein array on one support surface from a corresponding nucleic acid array on a separate surface, to protein arrays produced by the method, to uses of the protein arrays in the identification of interactions between arrayed proteins and other molecules, and to kits for producing said protein arrays.

An array is a precisely ordered arrangement of elements, allowing them to be displayed and examined in parallel (Emili, A. Q. and Cagney, G. (2000) Nature Biotechnology 18, 393-397). It usually comprises a set of individual species of molecules or particles arranged in a regular grid format wherein the array can be used to detect interactions, based on recognition or selection, with a second set of molecules or particles applied to it.

Arrays possess advantages for the handling and investigation of multiple samples. They provide a fixed location for each element such that those scoring positive in an assay are immediately identified, they have the capacity to be comprehensive and of high density, they can be made and screened by high throughput robotic procedures using small volumes of reagents and they allow the comparison of each assay value with the results of many identical assays.

The array format is well established for global analysis of nucleic acids, and oligonucleotide and cDNA arrays (DNA chips) are used for gene expression analysis. In a familiar format, large numbers (e.g. thousands) of DNA hybridization probes are attached in an ordered pattern to a surface such as nylon, glass or silicon and hybridized to fluorescently labeled whole cell mRNA or cDNA; the quantitative signals on each array element are measured in parallel by means of a reader device. The array approach may also be adapted for display of peptides and proteins; the elements displayed may be a set of related proteins or peptides, or the entire protein complement of an organism. Protein array technology allows high throughput screening for gene expression and molecular interactions. It is possible to use protein arrays to examine in parallel the functions of thousands of proteins previously known only by their DNA sequence.

Known uses of protein arrays include identification of antibodies and analysis of antibody specificity, measurement of global protein expression profiling, identification and quantitation of biomarkers, identification of ligand-receptor interactions, detection of protein modifications and protein-protein interactions, and screening and selecting proteins or ligands from libraries (Michaud, G. A. and Snyder, M. (2002) BioTechniques 33, 1308-13161).

Protein arrays are therefore powerful proteomics tools for large-scale parallel protein analysis, applicable to high throughput screening of protein activities and interactions. Protein arrays have the advantage of utilizing different sources of proteins and the arrays are often made by immobilization of recombinant proteins expressed from bacteria, yeast, baculovirus or cell-free systems. Nevertheless, protein availability often creates a significant production bottleneck, especially for species such as man. Moreover, unlike DNA arrays, protein arrays are difficult to store in a fully functional state over long periods of time due to protein deterioration.

WO 02/14860 (Discerna Limited) describes a 'Protein In Situ Array' (PISA) method in which an array surface comprising free or immobilized PCR DNA is used to template protein synthesis by a cell-free system, such as rabbit reticulocyte extract, and the proteins undergo simultaneous immobilization through a tag sequence which combines with a capture reagent which is also pre-coated on said array surface.

WO 02/059601 (President and Fellows of Harvard College) describes nucleic acid programmable protein arrays (NAPPA) for generating a protein array from a DNA array template, in which cloned plasmid DNA is immobilized on a glass slide wherein said slide is also coated with a protein-capturing antibody. A cell-free transcription/translation lysate is applied on the surface and the synthesized proteins are captured by the antibodies. This generates an in situ array in which the proteins are immobilized in the vicinity of their encoding DNA.

The NAPPA method comprises an array spot or location which includes a mixture of plasmid DNA, antibody and captured protein. This arrangement has the potential disadvantage of causing interference between the arrayed proteins and the co-localized DNA. Such interference is likely to cause a noisy signal during detection and could result in false positives. Furthermore, the NAPPA method permits only a single conversion of the DNA array, therefore, valuable DNA arrays must be discarded after just one use.

Thus, according to a first aspect of the invention, there is provided a method of producing a protein array which comprises exposing a nucleic acid array on a first support surface to a cell-free system, capable of performing protein synthesis by transcription and translation, such that the proteins expressed from said nucleic acid array are immobilized as a corresponding array on a second support surface.

According to a second aspect of the invention, there is provided a method of producing a protein array which comprises exposing a nucleic acid array on a first support surface to a cell-free system, capable of performing protein synthesis by transcription and translation, such that the proteins expressed from said nucleic acid array are immobilized as a corresponding array on a second support surface, characterized in that said second support surface is directly or indirectly in contact with said first support surface.

One advantage of the invention over known methods of producing protein arrays (e.g. PISA and NAPPA) is that multiple copies of a protein array may be produced from the same nucleic acid array template. For example, the nucleic acid array on the first support surface may be stored (because DNA is a stable molecule which can be stored indefinitely in dry form) and protein arrays may be produced 'on demand', as required, by repeated transcription and translation of the same nucleic acid array. This arrangement facilitates repeated screenings with different probes and avoids possible degradation and loss of function during storage. Proteins made as required in this way are more likely to retain their native conformation and functionality, being well hydrated on the array surface rather than dried. The invention therefore provides a repeatable method of preparing stably arrayed proteins.

A further advantage of the invention over the PISA and NAPPA methods is that the protein array is produced on a separate surface to the nucleic acid array. Therefore, the protein array may be removed from the nucleic acid array simply by removing the second support surface. Thus, 'pure' protein arrays may be produced from nucleic acid arrays, avoiding any possible interference from the co-localized nucleic acid.

A yet further advantage of the invention compared with the PISA method includes greater miniaturisation because nucleic acid arrays can be printed at high density and therefore allows highly parallel protein production in the array format. The invention also eliminates the need for liquid handling of nucleic acid/extract mixtures which are directly or indirectly in contact with said first support surface.

In one embodiment of the invention the protein capturing second support surface is directly or indirectly in contact with the nucleic acid bearing first support surface. The method of direct contact shall be referred to herein as the surface contact method. This requires application of the cell-free system, capable of performing protein synthesis by transcription and translation, to the first support surface (e.g. membrane) prior to contact with the second support surface (e.g. glass or second membrane).

Alternatively, indirect contact may be achieved by the presence of a protein permeable material, such as a membrane, placed between said first and second support surfaces. This method shall be referred to herein as the sandwich method.

The sandwich method constitutes one particular embodiment of the invention.

It will also be appreciated that the protein permeable material may be any rigid or semi-rigid material capable of being placed between the first and second support surfaces to permit free diffusion of proteins between said first and second support surfaces. In one embodiment, the protein permeable material is a membrane or other material comprising spaces or channels which limits lateral diffusion. In a further embodiment, the material will comprise apertures (e.g. spaces, holes or channels) which correspond to the position of the spots of each nucleic acid and protein on said first and second support surfaces of the array.

One advantage of the sandwich method is that the protein permeable material may contain the cell-free system capable of performing protein synthesis by transcription and translation. The cell-free system is applied to the protein permeable material where protein synthesis occurs, followed by diffusion of the protein and its immobilisation onto the second support surface. Thus, rather than a separate cell-free system application step, the cell-free system is applied by placing the protein permeable material onto the first support surface.

In one embodiment, the cell-free system is a cell-free lysate selected from a prokaryotic or eukaryotic system, such as *E. coli*, rabbit reticulocyte and wheatgerm or an artificially constructed system which enables protein synthesis in vitro.

In one embodiment, the first and second support surfaces are glass, plastic, nylon or other type of membrane and may optionally have a separate coating applied for enhancement of immobilizing the nucleic acid and/or the protein immobilizing agent.

It will be appreciated that references to nucleic acid herein, refer to any nucleic acid moiety capable of templating in vitro protein synthesis when exposed to a cell-free system comprising transcription and translation factors. In one embodiment, the nucleic acid array comprises genomic DNA, cloned DNA fragments, plasmid DNA, cDNA libraries, PCR products, synthetic oligonucleotides or mRNA. The nucleic acid constructs for in vitro transcription/translation may be obtained by PCR (polymerase chain reaction) or RT (reverse transcription)-PCR amplification, using primers designed on any known DNA sequences, such as those from databases and genome projects. In the embodiment wherein the nucleic acid array comprises an mRNA array, the cell-free system used to synthesise proteins is suitably an uncoupled cell-free system for translation only.

The nucleic acid may additionally comprise one or more transcriptional promoters, transcriptional regulatory sequences, untranslated leader sequences, sequences encoding cleavage sites, recombination sites, transcriptional terminators or ribosome entry sites. The nucleic acid may further comprise a plurality of cistrons (or open reading frames) or a sequence encoding a reporter protein whose abundance may be quantitated and can provide a measure of protein immobilized on the second support surface.

In a further embodiment of the invention said second support surface is pre-coated with a protein immobilization agent configured to attach (e.g. covalently or non-covalently) to either the expressed protein or an immobilization tag present on the expressed protein.

In one embodiment, the immobilisation tag is a polyhistidine sequence, such as hexahistidine and said protein immobilisation agent is a chelating agent such as Ni-NTA. In a further embodiment, said immobilisation tag is a peptide, domain or protein and said protein immobilisation agent is an antibody specific to said tag. In a yet further embodiment, said immobilisation tag is biotin and said protein immobilisation agent is a biotin-binding molecule, such as avidin.

In one embodiment of the invention said second support surface is precoated with a protein immobilization agent (e.g. an antibody) configured to attach (e.g. covalently or non-covalently) to the expressed protein.

According to a third aspect of the invention, there is provided a method of producing a protein array which comprises: (i) immobilizing protein-encoding DNA molecules, capable of being transcribed and translated by a cell-free system, on a first support surface; and (ii) placing a protein permeable material, carrying a cell-free system capable of performing protein synthesis by transcription and translation, between said first support surface and a second support surface carrying a protein immobilization agent; such that (iii) the proteins expressed from said DNA molecules become immobilized on said second protein immobilizing support surface as they are formed, to generate a corresponding protein array.

According to a further aspect of the invention, there is provided a method of producing a protein array which comprises: (i) immobilizing protein-encoding DNA molecules, capable of being transcribed and translated by a cell-free system, on a first support surface; (ii) applying a cell-free system, capable of performing protein synthesis by transcription and translation, to said first support surface; and (iii) placing said first support surface in contact with a second support surface carrying a protein immobilization agent; such that (iv) the proteins expressed from said DNA molecules become immobilized on said second protein immobilizing support surface as they are formed, to generate a corresponding protein array.

An advantage of using cell-free systems is that they provide an environment in which the conditions of protein synthesis can be adjusted and controlled through addition of exogenous biomolecules or molecules. This makes it possible to generate modified proteins, such as those with co- or post-translational modifications, non-natural or chemically modified amino acids (such as fluorescent groups).

Thus, in one embodiment of the invention, the cell-free system contains additional agents.

In one embodiment, the additional agents interact with the arrayed proteins or encode said interacting additional agents (e.g. nucleic acids capable of being transcribed and/or translated into protein by the cell-free system).

In a further embodiment, the additional agents are biomolecules or molecules required to produce modifications such as co- or posttranslational modifications, non-natural or chemically modified amino acids (such as fluorescent groups). In a yet further embodiment, the additional agents are reporter proteins such as an enzyme (e.g. β-galactosidase, chloramphenicol acetyl transferase, β-glucuronidase or the like) or a fluorescent protein (e.g. green fluorescent protein (GFP), red fluorescent protein, luciferase or the like). The additional agents are suitably added into the cell-free lysate, such that the resultant arrayed proteins are modified during translation or after immobilization and may allow the rapid detection of such proteins. In one embodiment, the additional agent comprises one or more protein folding promoting agents. These agents have the advantage of ensuring that the arrays consist of correctly folded proteins.

The invention can also be used for detection of protein interactions with other molecules such as proteins or smaller entities. Such interactions may occur via phosphorylation, methylation or proteolysis. The nucleic acid encoding potentially interacting soluble proteins may be incorporated within the cell-free system such that an interaction occurs between the synthesized proteins immobilized on the array and the soluble proteins synthesized at the same time by the cell-free system. Thus, according to a further aspect of the invention, there is provided a method for identifying interactions between arrayed proteins and one or more molecules which comprises: (i) immobilizing protein-encoding DNA molecules, capable of being transcribed and translated by a cell-free system, on a first support surface; (ii) placing a protein permeable material, carrying a cell-free system capable of performing protein synthesis by transcription and translation and containing said one or more molecules, between said first support surface and a second support surface carrying a protein immobilization agent; such that (iii) the proteins expressed from said DNA molecules become immobilized on said second protein immobilizing support surface as they are formed, to generate a corresponding protein array; and (iv) interactions of the arrayed proteins with said one or more molecules may be detected on the protein array.

This embodiment of the invention has the advantage of allowing localization of protein complexes on the protein array from which the interacting partners can be identified, leading to characterization of protein interaction networks. It will also be appreciated that this embodiment of the invention may also be used to identify a molecule that inhibits or enhances interactions with arrayed proteins.

In one embodiment of the invention, said one or more molecules are selected from antibodies, other proteins or domains, peptides, low molecular weight entities or ligands, cell extracts or nucleic acids.

In one embodiment, said one or more molecules comprise free DNA or mRNA capable of directing synthesis of one or more soluble proteins for interaction with the protein array either during or after translation.

An alternative embodiment for investigating protein-protein interactions is to generate nucleic'acid arrays co-spotted with a plurality (e.g. more than one) of different nucleic acid molecules, of which one of the encoded proteins can be immobilized by the protein-capturing surface.

This embodiment allows the proteins synthesised in situ from each spot to interact with each other. If they are interacting partners, they can be detected as a protein complex on the capturing surface and identified from the nucleic acid array.

A yet alternative embodiment for identifying interactions between the arrayed proteins and molecules, such as labeled ligands, proteins or nucleic acids, may be to directly expose said molecules to the protein array and detect binding to individual array locations by means of enzyme-coupled reaction, fluorescence, autoradiography or mass spectrometry. The arrays can thereby be used for direct screening of antibodies, ligands or protein interactions, etc. Such screening can be repeated several times because of the invention producing many identical copies of a single nucleic acid array.

Furthermore, by retaining the array format, the protein array surface may also be transferred to filters or plates pre-coated with target molecules such as antigens, and binding can be detected by labeled secondary reagents.

According to a further aspect of the invention, there is provided a protein array produced on a support surface by cell-free protein synthesis from a corresponding nucleic acid array template located on a separate support surface. In one embodiment, said support surface is either directly or indirectly in contact with said separate support surface.

According to a further aspect of the invention, there is provided a protein array produced on a support surface by cell-free protein synthesis from a corresponding nucleic acid array template located on a separate support surface, characterized in that said second support surface is directly or indirectly in contact with said first support surface.

According to a further aspect of the invention, there is provided a use of a protein array as defined herein to identify interactions of the arrayed proteins with one or more molecules selected from antibodies, other proteins or domains, peptides, low molecular weight entities or ligands, cell extracts or nucleic acids.

According to a further aspect of the invention, there is provided a use of a protein array as defined herein to identify interactions of the arrayed proteins with other molecules displayed in a library, such as a phage display or ribosome display library, in which the individual proteins are linked to encoding DNA or mRNA. In one embodiment, the ribosome display library is generated from DNA incorporated within the cell-free system used to synthesise the arrayed proteins. After binding to the array, interacting molecules are then identified by amplification and identification of the linked DNA or mRNA, for example by cloning phage or by PCR, RT-PCR, hybridisation or other methods.

According to a further aspect of the invention, there is provided a use of a protein array as defined herein to study cellular expression profiles.

According to a further aspect of the invention, there is provided a use of a protein array as defined herein to study post-translation modifications of cellular proteins.

According to a further aspect of the invention, there is provided a kit for producing a protein array which comprises: (i) a first support surface wherein said surface is suitable for having protein-encoding DNA molecules immobilized thereon; and (ii) a second support surface wherein said surface is suitable for having a protein immobilization agent immobilized thereon.

According to a further aspect of the invention, there is provided a kit for producing a protein array which comprises: (i) a first support surface wherein said surface is suitable for having protein-encoding DNA molecules immobilized thereon; and (ii) a second support surface wherein said surface is suitable for having a protein immobilization agent immobilized thereon, wherein said first and second support surfaces are configured to allow direct or indirect contact between said first and second support surfaces.

In one embodiment of this aspect of the invention, the kit additionally comprises a cell-free system, capable of performing protein synthesis by transcription and translation.

In a further embodiment of this aspect of the invention, the kit additionally comprises a microfluidic channeling system for delivering said cell-free system to said first support surface.

In a yet further embodiment of this aspect of the invention, the kit additionally comprises clamping means to ensure said first support surface remains in contact with said second support surface.

In a yet further embodiment of this aspect of the invention, the kit additionally comprises a protein permeable material, as defined herein, to be placed between said first and second support surfaces.

In a yet further embodiment of this aspect of the invention, the kit additionally comprises instructions to use said kit in accordance with the method as defined herein.

The invention will now be described, by way of example only, with reference to the accompanying drawings in which.

Figure 1:
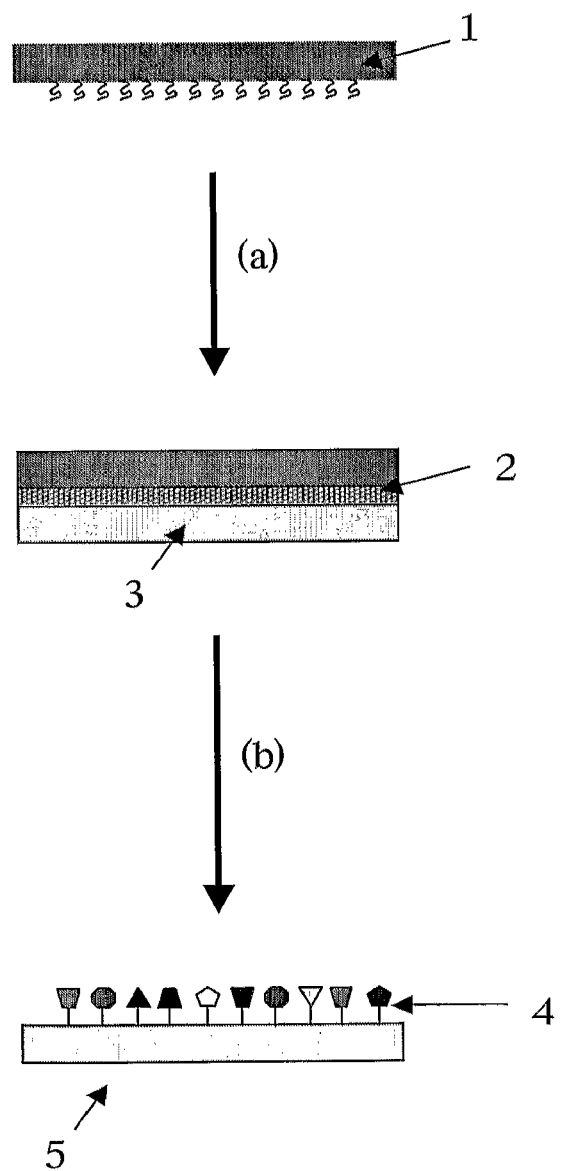
FIG. 1 shows a schematic diagram of how the sandwich method of the invention may be carried out.

Referring first to FIG. 1, the 'sandwich' embodiment of the invention comprises cell-free protein synthesis which occurs within a protein permeable material (e.g. membrane filter) placed between first and second support surfaces (e.g. glass slides). A first support surface (DNA array surface) 1 carries an array of immobilized DNA molecules while the second support surface 3 is coated with a protein-capturing reagent (protein capturing surface). As well as holding the cell-free extract, the membrane filter 2 may also function to restrict lateral diffusion of proteins. The filter is pre-soaked with a coupled cell-free lysate for protein synthesis; these may be *E. coli*, rabbit reticulocyte, or wheatgerm extracts in regular use for in vitro protein synthesis. Step (a) comprises assembly and combining of the DNA array surface 1, the membrane filter 2 and the protein capturing surface 3. Step (b) comprises cell-free protein expression and immobilization which may typically take 1-2 hours. The individual DNA molecules direct the synthesis of proteins 4, which subsequently diffuse through the filter to the second support surface 3 where they are immobilized in situ through interaction with the capturing reagent. Since protein diffusion within the plane of the membrane is limited under the conditions described, the location of protein spots on the protein array 5 is complementary to those on the DNA array, allowing ready identification of the proteins.

Figure 2:
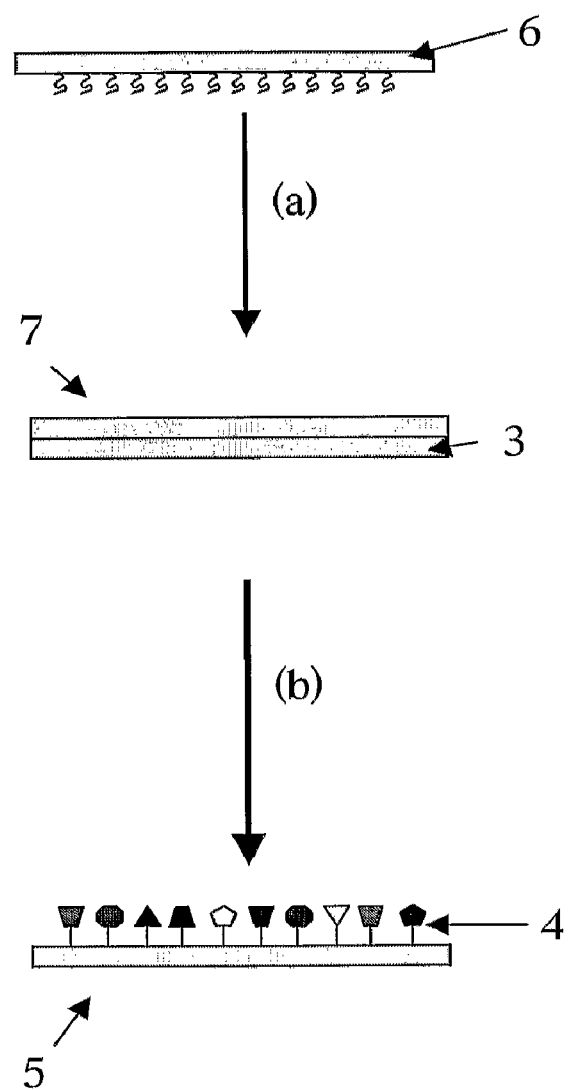
FIG. 2 shows a schematic diagram of how the surface contact method of the invention may be carried out.

FIG. 2 illustrates the 'surface contact' embodiment of the invention and comprises DNA molecules immobilized as an array on a first support surface 6 (e.g. membrane surface, such as a hybridisation membrane designed for nucleic acid detection). This DNA array is soaked in the cellfree extract containing protein synthesis components 7 and step (a) comprises bringing the first support surface 6 into direct contact with the second protein immobilizing support surface 3, e.g. glass slide or membrane, pre-coated with the protein-capturing reagent. Step (b) comprises cell-free protein synthesis and immobilization (typically for 1-2 5 hours) which is allowed to occur at the boundary between the membrane and the protein-immobilizing surfaces, with the proteins 4 becoming immobilized as a protein array 5 as described for the sandwich method described above.

EXAMPLES

Materials and Methods

1. Materials

Oligonucleotide primers (RTST7/B: 5'-GATCTCGATC-CCGCG-S' (SEQ ID NO: 1), Cy5-coupled RTST7/B: 5' Cy5-GATCTCGATCCCGCG-3' (SEQ ID NO: 2) and $NH_2$-coupled terminator/F: 5'$NH_2$-AAAACCCCTCAAGACCCG-3' (SEQ ID NO: 3)) were obtained from Sigma-Genosys, UK. Plasmid encoding GFP was obtained from Roche, UK. Nexterion™ slide H (Hydrogel coated) and Nexterion™ slide E (Epoxysilane coated) were obtained from SCHOTT Nexterion. Slides coated with nickel chelate for polyhistidine binding were obtained from XENOPORE. Rabbit reticulocyte lysate TNT was obtained from Promega and *E. coli* S30 extract was either synthesised according to known procedures or purchased from Roche, UK. Maxisorp™ slides for protein coating were obtained from Nunc, UK.

2. Methods 2.1 PCR Constructs for DNA Immobilization

Standard PCR methods were used to produce PCR constructs for cell-free protein synthesis. A double-(His)6 tag was fused at the C-terminus of the target protein for protein immobilization (WO 02/14860). Labeling of DNA fragments was performed by PCR using modified primer(s) with the required chemical group. For DNA immobilization, the 3' primer (NH2—coupled terminator IF, see materials) labeled with an amino (NH2) group at the 5' end was used. For both DNA detection and immobilization, the Cy5-coupled primer RTST7/B and the NH2-coupled terminator/F were used. After 30 cycles, the labeled PCR products were analyzed using agarose gel electrophoresis and purified using Gene-Elute PCR clean-up kit (Sigma) to remove excess 3' primer. DURAPORE® membrane filters (0.22 flm) were obtained from Millipore, UK.

2.2 DNA Immobilization

Immobilization of DNA on glass slides was carried out using either Nexterion™ slide H or Nexterion™ slide E using the manufacturer's instruction with slight modifications. In brief, for Nexterion™ slide H, NH2-labelled PCR fragments (100-200 ngIIII) were mixed with a 6× printing buffer (300 mM sodium phosphate pH 8.5) at a ratio of 5:1 (PCR fragment: 6× printing buffer). The mixture was then spotted onto a glass slide and incubated in a humidified chamber box at room temperature overnight. For Nexterion™ slide H, the slides were blocked by submerging into blocking solution (O.1M Tris-HCl, 50 mM ethanolamine, pH 9.0) for 1 hr at room temperature. After three washes with sterilized water, the slides were dried by centrifugation at 200×g for 5 min, followed by storage at 4° C. For Nexterion™ slide E, after printing DNA as above, the slides were incubated at 60° C. for 30 min and washed once with 0.1% Triton X-100 for 5 min, twice with 1 mM HCl for 2 min, once with 100 mM KCl for 10 min, and once with H20 for 1 min. The slides were blocked with the blocking solution at 50° C. for 15 min followed by washing with H20 for 1 min, dried as above and stored at 4° C.

For DNA immobilization on Hybond™ N+ membranes, plasmid DNA or PCR fragments with or without $NH_2$ labeling were spotted onto the surface of Hybond™ N+ membranes. After brief drying, the membranes were incubated at 80° C. for 2 hrs; alternatively they were treated by UV crosslinking (Auto crosslinking setting, 120 mJ/cm$^2$, UV Stratalinker 3600). The membranes were then dried and stored at 4° C.

2.3 Sandwich Arraying

A Millipore DURAPORE® membrane filter was first soaked with *E. coli* cellfree lysate (25~1 lysate per cm2). It was then placed between the two surfaces (DNA array slide and the protein capturing slide) and a tight contact between the surfaces was made. After incubation at 30° C. for 1-4 hrs (depending on the cell-free system used), the slides were separated and the protein-capturing surface was washed three times with PBS containing 0.05% TWEEN®.

2.4 Surface Contact Arraying

A Hybond™ N+ membrane (Amersham, UK) carrying immobilized DNA was placed in contact with a surface (e.g. membrane or glass slide) precoated with a protein-capturing reagent. Cell-free protein synthesis was started by spreading a coupled cell-free lysate onto the non-DNA coated side of the membrane carrying the DNA array. To create a close contact, a glass slide was placed over the Hybond™ membrane and secured to the second surface. The conditions for cell-free protein synthesis and immobilization were as described in section 2.3 above.

2.5 Slide Scanning

Detection of Cy5 and Cy3 was carried out using an Affymetrix 428 array scanner. Image analysis was Imagene™ 4.0 (BioDiscovery, Inc.)

Example 1

Generation of a GFP Array by the Sandwich Method

Figure 3:
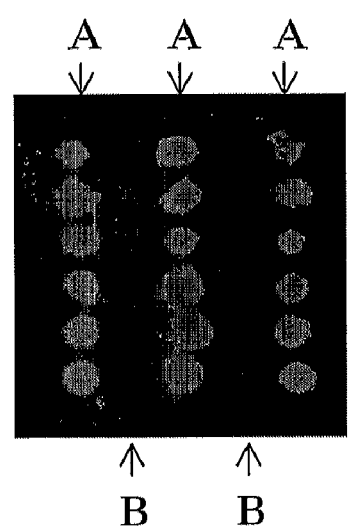
FIG. 3 shows the results of a protein detection assay following the production of a single protein array from a single nucleic acid array using the sandwich method.

PCR fragments encoding a double-(His)$_6$ tagged wild-type Green Fluorescent Protein GFP (Roche) were immobilized on a Nexterion™ slide H. As a control, PCR fragments encoding a single-chain V H/K antibody fragment were immobilized on the same slide. A Ni-NTA coated slide was used as the protein-capturing surface. A membrane filter (Millipore DURAPORE®) pre-soaked with *E. coli* cell-free extract (Roche, UK) was inserted between the two surfaces. After incubation at 30° C. for 1.5 hrs, the Ni-NTA coated slide was washed three times with PBS containing 0.1% TWEEN® 20. The slide was probed with biotinylated antiGFP antibody (Abcam, Cambridge, UK) (1:4000) followed by horseradish peroxidase (HRP)-linked streptavidin (1:4000). The HRP was developed by fluorescence-based detection using a tyramide-Cy3 substrate (Perkin Elmer Life Science, UK). FIG. 3 demonstrates the results of the GFP array, probed by anti-GFP, followed by fluorescence based detection (Cy3). Lane A shows that GFP was detected as an array corresponding to the pattern of the immobilized DNA, while the control single-chain antibody fragment (VH/K) in Lane B was negative with anti-GFP.

Example 2

Demonstration of Repeated Use of the Same DNA Array to Create Protein Arrays

Figure 4:
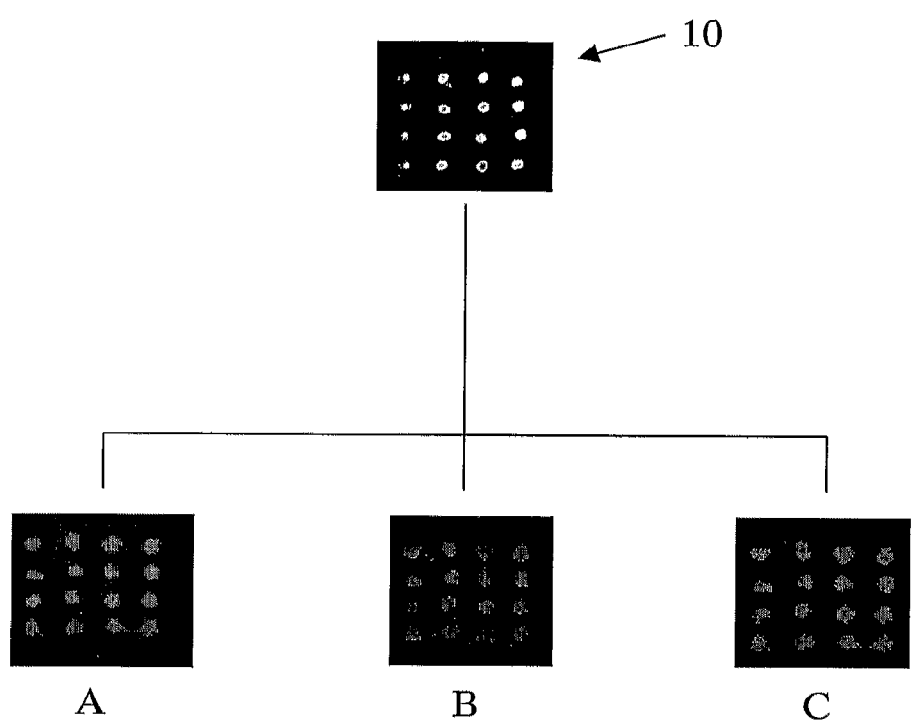
FIG. 4 shows the results of a protein detection assay following the production of three copies of protein arrays from a single nucleic acid array using the sandwich method.

PCR was carried out on the GFP plasmid template using the modified primers (NH$_2$-coupled terminator/F and Cy5-coupled RTST7/B, see Materials). This produced labeled PCR fragments with an NH2 group at one end and Cy5 at the other. The coupled NH2 group was used to immobilize the PCR fragments on a Nexterion™ slide H using the procedure as described in Example 1. As the immobilized PCR fragment contained a Cy5 group, it could be scanned and detected on the slide, revealing the arrayed DNA spots (shown as feature 10 in FIG. 4). The slide carrying the DNA array was then subjected to the sandwich method to generate a GFP protein array, which was detected using anti-GFP antibody as in Example 1. FIG. 4 shows the resultant GFP array (shown as array A), which has a very similar pattern to that of the DNA array. To demonstrate reuse of the DNA array, the sandwich procedure was repeated using the same DNA array as a template. This produced a second and third copy of the GFP array (arrays B and C, respectively in FIG. 4), confirming that a single DNA array template can be used repeatedly to generate protein arrays using this process.

Example 3

Generation of a TIMP-1 Array by the Sandwich Method

Figure 5:
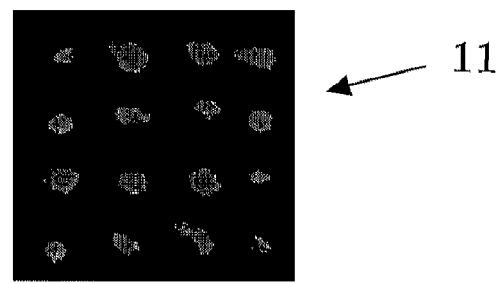
FIG. 5 shows the results of a protein detection assay following the production of a single protein array from a single nucleic acid array using the sandwich method.

A PCR fragment encoding double-(His)6 tagged TIMP-1 (Tissue Inhibitor of MetalloProteinase 1) was constructed as described for GFP. DNA immobilization was carried out as described in Example 1 and a Ni-NTA coated slide was used to capture the protein. Following the sandwich array procedure, with incubation at 30° C. for 4 hours, the Ni-NTA slide was probed by anti-His antibody (1:4000) (Sigma, UK). The results demonstrate that TIMP-1 was detected with the same array pattern as the DNA array (see array 11 in FIG. 5).

Example 4

Figure 6:
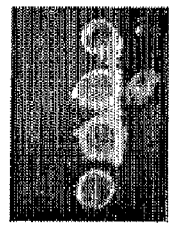
FIG. 6 shows the results of a protein detection assay following the production of a single protein array on a ligand-coated slide from a single nucleic acid array using the sandwich method.

Generation of a Protein Array on Ligand (MMP-2)-Coated Slides by the Sandwich Method Matrix Metalloproteinase (MMP-2), a ligand for TIMP-1, was used to coat a Nunc Maxisorp™ slide (3 µg/ml) following the manufacturer's protocol. This ligand-coated surface was used to capture TIMP-1 synthesized from a DNA array. In this way, only proteins with that specific ligand-binding activity are detected, leading to direct screening of functional binding activity and specificity. Double-(His)$_6$ tagged GFP was used as a negative control. After the sandwich arraying procedure with 4 hours incubation, the MMP-2 coated slide was probed with anti-His antibody. FIG. 6 demonstrates the results of the TIMP-1 array, probed by anti-His antibody followed by fluorescence based detection (Cy3). Lane B shows that TIMP-1 was strongly detected as an array corresponding to the pattern of the immobilized DNA, while the double-(His)$_6$ tagged GFP control in Lane A did not demonstrate binding.

Example 5

Figure 7:
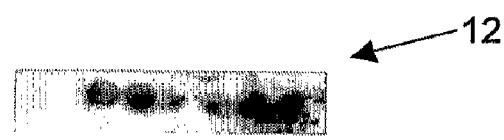
FIG. 7 shows the results of a protein detection assay following the production of a single protein array from a single nucleic acid array using the surface contact method.

Generation of a GFP array by the surface contact A plasmid encoding double-(His)$_6$ tagged GFP was immobilized on a Hybond N+ membrane and the DNA surface placed over a nitrocellulose surface pre-conjugated with a monoclonal anti-His antibody (5 µg/ml). *E. coli* cell-free lysate from Roche was applied and the membranes were placed between two glass slides and clipped securely together. After incubation at 30° C. for 3 hrs, the nitrocellulose membrane was probed with biotinylated anti-GFP followed by HRP-linked streptavidin. The HRP was developed by chemiluminescence, which detected GFP at positions corresponding to the DNA spots (shown as feature 12 in FIG. 7).

The invention claimed is:

1. A method of producing a protein array, comprising:
   a) exposing a nucleic acid array immobilized on a first support surface to a cell-free system wherein the cell-free system is capable of performing protein synthesis by transcription and translation;
   b) expressing a plurality of proteins from said nucleic acid array; and
   c) immobilizing said proteins as a corresponding array on a second support surface, characterized in that said second support surface is directly in contact with said first support surface or said first and second support surfaces are configured to be of such proximity to ensure that the proteins are immobilized on said second support surface as they are formed;
   wherein the first and second support surfaces are selected from the group consisting of a slide and a membrane.

2. The method of claim 1, wherein a protein permeable material is between said first support surface and said second support surface.

3. The method of claim 2, wherein said protein permeable material contains a cell-free system capable of performing protein synthesis by transcription and translation.

4. The method of claim 3, wherein said cell-free system is a cell-free lysate selected from the group consisting of a prokaryotic system and a eukaryotic system.

5. The method of claim 1, wherein said nucleic acid array is selected from the group consisting of genomic DNA, cloned DNA fragments, plasmid DNA, cDNA libraries, PCR products, synthetic oligonucleotides and mRNA.

6. The method of claim 1, wherein said second support surface is pre-coated with a protein immobilization agent configured to covalently or non-covalently attach to the expressed proteins.

7. The method of claim 6, wherein said protein immobilization agent is an antibody.

8. The method of claim 1, wherein said second support surface is pre-coated with a protein immobilization agent configured to covalently or non-covalently attach to an immobilization tag present on the expressed proteins.

9. The method of claim 8, wherein said immobilization tag is a polyhistidine sequence and said protein immobilization agent is a chelating agent.

10. The method of claim 9, wherein said polyhistidine sequence is hexahistidine.

11. The method of claim 9, wherein said chelating agent is Ni-NTA.

12. The method of claim 8, wherein said protein immobilization agent is an antibody specific to said immobilization tag and said immobilization tag is selected from the group consisting of a peptide, a peptide domain and protein.

13. The method of claim 8, wherein said immobilization tag is biotin and said protein immobilization agent is a biotin-binding molecule.

14. The method of claim 2, wherein the protein permeable material between said first support surface and said second support surface is a protein permeable membrane.

15. The method of claim 14, wherein the protein permeable membrane has apertures corresponding to positions of said immobilized proteins.

* * * * *

SEQUENCE LISTING

<160> NUMBER OF SEQ ID NOS: 3

<210> SEQ ID NO 1
<211> LENGTH: 15
<212> TYPE: DNA
<213> ORGANISM: Artificial
<220> FEATURE:
<223> OTHER INFORMATION: Synthetic Primer

<400> SEQUENCE: 1
gatctcgatc ccgcg                                                    15

<210> SEQ ID NO 2
<211> LENGTH: 15
<212> TYPE: DNA
<213> ORGANISM: Artificial
<220> FEATURE:
<223> OTHER INFORMATION: Synthetic Primer
<220> FEATURE:
<221> NAME/KEY: Cy5
<222> LOCATION: (1)..(1)
<223> OTHER INFORMATION: Cy5 labelled nucleotide

<400> SEQUENCE: 2
gatctcgatc ccgcg                                                    15

<210> SEQ ID NO 3
<211> LENGTH: 18
<212> TYPE: DNA
<213> ORGANISM: Artificial
<220> FEATURE:
<223> OTHER INFORMATION: Synthetic Primer
<220> FEATURE:
<221> NAME/KEY: NH2_coupled_terminator
<222> LOCATION: (1)..(1)
<223> OTHER INFORMATION: NH2 coupled to 5' nucleotide

<400> SEQUENCE: 3
aaaacccctc aagacccg                                                 18